US010954179B1

(12) United States Patent
Ghorbani

(10) Patent No.: US 10,954,179 B1
(45) Date of Patent: Mar. 23, 2021

(54) METHOD AND APPARATUS FOR FILTERING HEAT TRANSFER FLUID FROM A MONOETHYLENE GLYCOL STREAM

(71) Applicant: SCHLUMBERGER TECHNOLOGY CORPORATION, Sugar Land, TX (US)

(72) Inventor: Nasser Ghorbani, Houston, TX (US)

(73) Assignee: CAMERON INTERNATIONAL CORPORATION, Houston, TX (US)

( * ) Notice: Subject to any disclaimer, the term of this patent is extended or adjusted under 35 U.S.C. 154(b) by 0 days.

(21) Appl. No.: 16/553,639

(22) Filed: Aug. 28, 2019

(51) Int. Cl.
*C07C 29/80* (2006.01)
*B01D 3/14* (2006.01)
*C07C 29/76* (2006.01)
*B01D 39/16* (2006.01)

(52) U.S. Cl.
CPC .............. *C07C 29/80* (2013.01); *B01D 3/143* (2013.01); *B01D 39/1692* (2013.01); *C07C 29/76* (2013.01)

(58) Field of Classification Search
CPC ......... C07C 29/76; C07C 29/80; B01D 3/143; B01D 39/1692
See application file for complete search history.

(56) References Cited

U.S. PATENT DOCUMENTS

| 6,582,552 | B1 * | 6/2003 | Juhola | B01D 3/06 |
| | | | | 159/29 |
| 7,232,505 | B2 * | 6/2007 | Laborie | C07C 29/76 |
| | | | | 203/18 |
| 9,006,500 | B2 * | 4/2015 | Moen | B01D 1/225 |
| | | | | 568/868 |
| 9,089,790 | B2 * | 7/2015 | Phelps | B01D 15/00 |
| 9,433,875 | B2 * | 9/2016 | Phelps | B01D 15/36 |
| 9,926,250 | B2 * | 3/2018 | Arumugam | C07C 29/76 |
| 10,471,366 | B2 * | 11/2019 | Zheng | B01D 1/0064 |
| 2014/0256990 | A1 * | 9/2014 | Moen | F26B 17/20 |
| | | | | 568/868 |
| 2014/0373715 | A1 | 12/2014 | Alper | |
| 2017/0015613 | A1 * | 1/2017 | King | C07C 29/80 |
| 2017/0368471 | A1 * | 12/2017 | Zheng | B01D 1/0094 |

FOREIGN PATENT DOCUMENTS

| CN | 106006835 | A | | 10/2016 | | |
| KR | 1020180089762 | A | | 8/2018 | | |
| WO | WO-2007073204 | A1 | * | 6/2007 | ............ | C07C 29/80 |
| WO | 2015198212 | A1 | | 12/2015 | | |

OTHER PUBLICATIONS

International Search Report and Written Opinion issued in PCT Application PCT/US2020/048168, dated Dec. 7, 2020 (15 pages).

* cited by examiner

*Primary Examiner* — Jonathan Miller
(74) *Attorney, Agent, or Firm* — Hauptman Ham, LLP; Ronald G. Embry, Jr.

(57) ABSTRACT

Methods and apparatus for reclaiming monoethylene glycol from a produced hydrocarbon stream are described. The method includes directly contacting a stream containing monoethylene glycol (MEG) with a heat transfer fluid, vaporizing the MEG by transferring heat from the heat transfer fluid to the MEG to produce a vapor stream, liquefying the vapor stream to form a liquid stream, passing the liquid stream through a filter comprising an oleophilic material, and removing residual heat transfer fluid from the liquid stream using the filter.

20 Claims, 3 Drawing Sheets

METHOD AND APPARATUS FOR FILTERING HEAT TRANSFER FLUID FROM A MONOETHYLENE GLYCOL STREAM

FIELD

Embodiments disclosed herein generally relate to recovery of chemical additives in oil and gas processing. Specifically, methods and apparatus for reclamation of monoethylene glycol from a produced stream are described.

BACKGROUND

In oil and gas production, management of methane hydrates is a challenge. In certain temperature and pressure regimes common during oil and gas production and transportation, methane coordinates with water to produce methane hydrates, which appear as a crystalline solid and can disrupt fluid flow in pipelines, pumps, and compressors. Many methods are used to inhibit and/or counteract the formation of methane hydrates in produced streams. One such method is to use a chemical additive to inhibit formation of methane hydrates. The most commonly used such additive is monoethylene glycol ("MEG"). MEG changes the temperature range at which hydrates form so that the operating temperature of the system does not promote hydrate formation.

Relatively large amounts of MEG must be used to achieve useful results, and MEG is expensive in large quantities. Thus, reclaiming and recycling MEG is economically attractive. Typical processes for reclaiming MEG from produced streams involve flashing MEG, along with water, from the produced stream and then distilling the MEG/water mixture to recover MEG. The flashing process involves vaporizing MEG by contacting the MEG with a heat transfer fluid ("HTF"). The vaporization process may be performed at temperatures and pressures that result in rapid vaporization of MEG. The vaporization can be so rapid, in some cases, that small amounts of the heat transfer fluid can be entrained in the flashing vapor and can contaminate the reclaimed MEG, resulting in a need for further purification processing. There is a need for methods and apparatus to reclaim MEG while minimizing contamination.

SUMMARY

Embodiments described herein provide a method, comprising directly contacting a stream containing monoethylene glycol (MEG) with a heat transfer fluid (HTF); vaporizing the MEG by transferring heat from the HTF to the MEG to produce a rich MEG stream; condensing the rich MEG stream; passing the rich MEG stream through a filter comprising an oleophilic material; and removing residual HTF from the liquid stream using the filter to form a clean MEG stream.

Other embodiments described herein provide a method, comprising mixing a MEG concentrate stream with an HTF to form a vaporization mixture; vaporizing a rich MEG stream from the vaporization mixture in a vessel; passing the rich MEG stream through a filter comprising a filter material selective to the HTF in a filter flow direction; immobilizing the HTF on the filter material to form a clean MEG stream; detecting an amount of the HTF in the clean MEG stream; determining a filter efficiency based on the amount of the HTF in the clean MEG stream; determining an end point based on the filter efficiency; and upon determining the end point, flushing the filter material by flowing a low polarity aprotic solvent through the filter in a flush flow direction.

Other embodiments provide a method, comprising mixing a MEG concentrate stream with an HTF to form a vaporization mixture; vaporizing a rich MEG stream from the vaporization mixture in a vessel; passing the rich MEG stream through a plurality of filters comprising a filter material selective to the HTF in a filter flow direction; recycling a portion of the rich MEG stream through one or more of the plurality of filters; immobilizing the HTF on the filter material to form a clean MEG stream; detecting an amount of the HTF in the clean MEG stream; determining a filter efficiency based on the amount of the HTF in the clean MEG stream; determining an end point based on the filter efficiency; and upon determining the end point, flushing the filter material by flowing a low polarity aprotic solvent through the filters in a flush flow direction.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

To remove residual HTF from a MEG stream recovered in a vaporizer, the HTF may be filtered from the MEG stream using a filter material with selective affinity for the HTF. When the HTF is a hydrocarbon material, the filter material may be an oleophilic material. The oleophilic material will selectively attract and immobilize the hydrocarbon material from the passing stream onto the filter.

Figure 1:
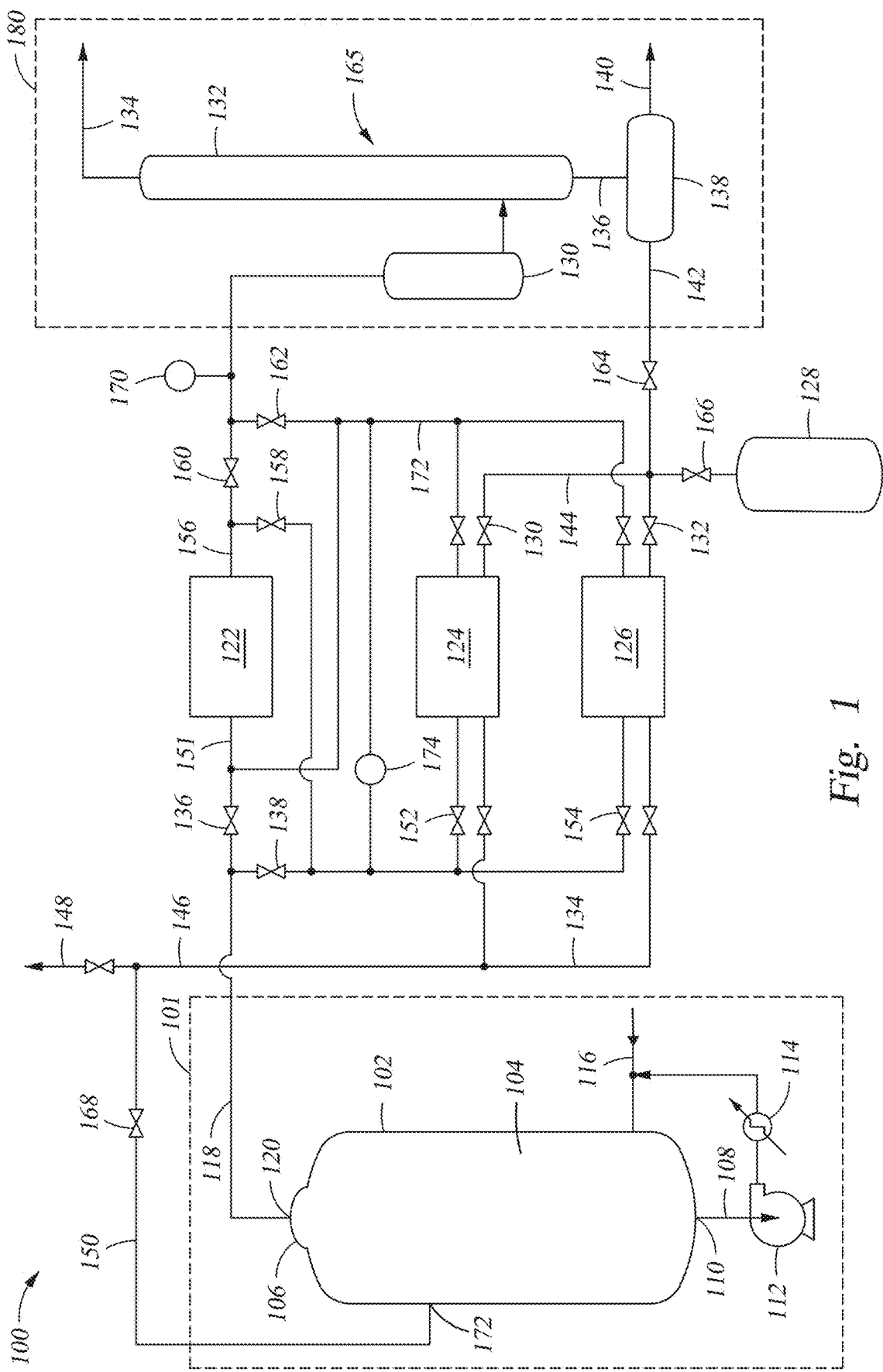
FIG. 1 is a process diagram of an apparatus according to one embodiment.

FIG. 1 is a process diagram of an apparatus 100 according to one embodiment. The apparatus 100 includes a vaporization section 101. The vaporization section 101 includes a vaporization vessel 102 with a liquid section 104 and a vapor section 106. A recirculation line 108 is coupled to a bottom part 110 of the liquid section 104. A pump 112 may be used to recirculate liquid to the liquid section 104. A heat exchanger 114 is used to maintain temperature of an HTF circulated through the recirculation line 108. A feed line 116 adds a feed stream to the recirculation line 108 for vaporization processing. The feed stream is generally a MEG concentrate stream from a well gas processing facility. The HTF is heated to a temperature that will vaporize at least a portion of the feed stream in the vessel 102. The vapor rises from the liquid section 104 to the vapor section 106, forming a rich MEG stream containing primarily MEG and water. Impurities remaining in the HTF are removed by other processing.

The HTF is typically a material that is immiscible with glycol. It should be noted that the apparatus and methods described herein, used primarily for recovery of MEG from a hydrocarbon processing facility, can be used in recovery of other related glycols, such as diethylene glycol and triethylene glycol. Materials typically used as HTF materials in these processes can be hydrocarbons with low volatility to minimize vaporization in the vaporization section. Materials such as $C_9$-$C_{13}$ hydrocarbons, of any linear, branched, cyclic, aromatic, paraffinic, polycyclic, or polyaromatic variety can be used. Some long-chain fatty acids, esters, and ethers can also be used, for example palm oil derivatives.

A vapor line 118 is coupled to a top part 120 of the vapor section 106 to relieve vapor from the vaporization section 101. The vapor line 118 is coupled to a liquefier 122 and to a filter 124. The liquefier 122 and filter 124 are configured such that the rich MEG stream in the vapor line 118 can be directed to the liquefier 122 before flowing to the filter 124, or the vapor can be sent directly to the filter 124 before flowing to the liquefier 122. The liquefier 122 liquefies at least a portion of the rich MEG stream in the vapor line 118. The liquefier 122 may be a condenser, a distillation column, or other device that can liquefy gases.

The filter 124 contains a filter material that is oleophilic. The oleophilic material preferentially adsorbs hydrocarbon materials or materials with significant hydrocarbon content. Such materials may also be hydrophobic. Materials useful as filter materials in this regard are usually at least about 90% by mass carbon and hydrogen. Many such materials are essentially 100% by mass carbon or 100% by mass carbon and hydrogen. Many organic polymers can be used. Polyolefins such as polypropylene and polystyrene have sufficiently oleophilic properties to be used for the filter element. Hetero-polymers can also be used. For example, silicones, polypyrroles and polyimides, styrenic resins, polyaromatic materials, polyesters, polyacrylates, and carbon materials such as graphite and activated carbon can be used. The polymer can be aromatic or aliphatic. Mixtures of the above can also be used. Generally, the material used for the filter is selective to the molecules of the HTF. In one embodiment, the filter element is made of a polystyrene resin, such as AMBERLITE® resin, for example XAD-4 or XAD-7, available from Dow Chemical Co. of Midland, Mich.

The filter 124 can be configured in any convenient way. The material to be filtered may be forced to flow through a powder cake of the filter material, or the filter material may be structured as a filter element insert that fits into a housing. For example, a woven fiber filter element using fibers made of, or coated with, the above materials may be used. In other embodiments, the filter material may be supported and fluidized within a filter housing. The filter material has pore size selected to adsorb or allow permeation of the molecules used as HTF, with high surface area. In general, the highest surface area available for the selected pore size is most useful.

The filter 124 may be configured as a gas filter or a liquid filter. In FIG. 1, the filter 124 and liquefier 122 are structured such that the vapor from the vapor line 118 can be routed to the filter 124 before the liquefier 122, or the vapor may be routed to the liquefier 122 before the filter 124. When operating in liquid-contact mode the filter 124 can be operated liquid-full, or with some gas space.

Residual HTF is scavenged by the oleophilic filter material in the filter 124 and deposits on the surface of the filter material. As the surface of the filter material is occupied by adsorbed HTF, the filter effectiveness in removing HTF from the rich MEG stream flowing in the line 118 declines due to reduction in absorptive sites on the surface of the filter material. The filter effectiveness can be defined according to incoming and outgoing concentration of HTF in the flowing fluid. Removal of HTF can be defined as a ratio $(F_i-F_o)/F_i$. As HTF removal by the filter declines, $F_o$ approaches $F_i$, and the ratio approaches zero. Concentration of HTF in the stream can be ascertained by any convenient means, such as chromatography or spectroscopy. A threshold can be defined to mark an end point of filter performance. Alternately or additionally, pressure drop through the filter may indicate adsorption in the filter is reducing material transport, and therefore filter effectiveness. When the filter 124 reaches the threshold, the filter 124 can be bypassed, with none of the vapor stream 118 going to the filter 124, so that the filter element can be changed. A second filter 126 may be provided to allow continued filtration while one filter element is changed. In such cases, the filter 124 is a first filter, and while the filter element in the first filter is changed, the second filter 126 is placed into service. When the filter element in the second filter 126 subsequently needs to be changed, the first filter 124, with newly changed filter element, can be placed into service.

When performance of the filter element has become degraded through use, the filter material can be regenerated by removing the hydrocarbon adsorbed thereon. To do this, a solvent miscible with the hydrocarbon but not readily adsorbed by the filter element may be used. In many cases, low polarity aprotic solvents can be used to remove the HTF from the filter element readily. Such solvents include aprotic solvents having dipole moment of 1.5 Debye or less. Some low polarity aprotic solvents can dissolve polymers, so a low polarity aprotic solvent with low solvent power relative to the filter material is generally selected. Examples of low polarity aprotic solvents that may be used include medium vapor pressure hydrocarbons such as linear, branched, and cyclic pentanes, hexanes, heptanes, octanes, and nonanes; aromatic hydrocarbons such as benzene, toluene, and xylene; hetero-organic compounds such as dioxane, anisole, dimethylamine, diethyl ether, methyl t-butyl ether; halogenated aliphatic compounds such as chloromethane, dichloromethane, chloroform, and carbon tetrachloride. Polar miscible co-solvents such as methanol, propanol, and acetone may also be used.

In some cases, a flush system can be provided to flush the filter element (or elements in the case where multiple filter units are used) without removing the filter element from the filter. In FIG. 1, a flush source 128 is fluidly coupled to each of the filters 124 and 126 by a flush line 144, with isolation valves 130 and 132 provided to route flush material to respective filters 124 and 126. In this case, the flush system is arranged to counter-flow flush fluid through the filters 124 and 126 in a direction opposite from the flow direction of MEG with impurities. The flush system can alternately be arranged to co-flow flush fluid through the filters 124 and 126 in the same flow direction as MEG with impurities. The flush fluid can be lined up through one or both of the filters 124 and 126 by operating the valves 130 and 132. In the case where one filter is in operation while another is being flushed, one of the valves 130 and 132 can be open while the other is closed. Flush fluid exits the filters 124 and 126 through flush exit manifold 134 into flush outlet line 146. The flush fluid can then be routed to any convenient disposal through flush exhaust line 148. In general, the rich MEG flows through the filters 124/126 in a filter flow direction, and the flush material flows through the filters 124/126 in a flush flow direction. The filter flow direction can be the same as the flush flow direction, or different. For example, the flush flow direction can be opposite to the filter flow direction or transverse to the filter flow direction.

As noted above, the MEG stream from the vaporizer can be routed through the vapor line 118 directly to the liquefier 122 by opening liquefier line-up valve 136 and closing filter line-up valve 138. In such configurations, rich MEG flows through the vapor line 118 to an inlet 151 of the liquefier 122. The filter line-up valve 138 allows the MEG stream to flow directly to the filters 124 and 126, as determined by first filter inlet valve 152 positioned at the inlet of the first filter 124, and second filter inlet valve 154 positioned at the inlet of the second filter 126. In this scenario, after filtration has removed the HTF impurities in the MEG stream to form a clean MEG stream containing water, the clean MEG stream is routed to the liquefier inlet 151. Output of the two filters 124 and 126 is combined here into one stream, which can be routed to two locations. Note that in most cases, only one filter 124/126 will be in use at any time while the other filter is being maintained, either by flushing or replacing filtration media. The filter output can be routed directly to the liquefier inlet 151 or to a location upstream of the liquefier 122, if the vapor line 118 was lined up directly to the filters 124/126. Alternately, the filter output can be routed to the liquefier outlet 156, or to a location downstream of the liquefier outlet 156, if the vapor line 118 was lined up directly to the liquefier inlet 151. As noted above, the vapor line 118 can be lined up directly to one or the other destination by operation of the liquefier line-up valve 136 and the filter line-up valve 138.

If the vapor line 118 is lined up directly to the liquefier inlet 151, the rich MEG stream, containing water and HTF impurities, flows through the liquefier 122 and is converted, as least mostly, to liquid from vapor. The outlet 156 of the liquefier 122, containing mostly liquid, can be routed to the filters 124/126, both together or one individually, by opening filter liquid feed valve 158 and closing liquefier outlet block valve 160. The liquefier outlet 156 is thus lined up to flow directly to one of the filters 124/126, depending on the status of the filter inlet valves 152/154. The filter outlet, in this case, can be routed back to the liquefier outlet 156 at a location downstream of the liquefier outlet block valve 160 to subsequent processing by opening the downstream filter outlet valve 162.

A clean MEG stream is output from the filters 124/126 in clean MEG line 172, which can be routed to the liquefier inlet 151 or liquefier outlet 156, as described above. The filtered, liquefied clean MEG stream, containing water, is routed to a purification section 180. The purification section 180 includes a holding vessel 130 and a MEG/water separation unit 165, which in turn comprises a distillation column 132, and a MEG collection vessel 138. The holding vessel 130 is primarily used to feed the distillation column 132. The distillation column 132 separates the MEG and water into an overhead water stream 134 and a bottoms MEG stream 136. The degree of separation of MEG and water in the MEG/water separation unit 165 is dependent on known distillation design principles. The overhead water stream 134 can be routed to any convenient subsequent disposal. The bottoms MEG stream 136 is collected in the MEG vessel 138, where a first portion can be recovered as a purified MEG stream 140 while a second portion 142 can be used as part of the flush system for the filters 124/126. As described above, a flush source 128 provide a flush material for use in flushing the filters 124/126. The purified MEG can be used as a final flush of the filters 124/126 to remove any impurities not removed by the flush material in the flush source 128, and also to remove flush material if desired. A MEG flush valve 164 can be opened to flow purified MEG from the MEG vessel 138 to the flush line 144. A flush line block valve 166 can be closed to prevent intrusion of MEG into the flush source 128. The filter flush valves 130 and 132 are operated, as above, to direct flush MEG through the respective filters 124/126.

Typically, MEG flush will be used following flushing from the flush source 128 to minimize use of purified MEG. When purified MEG from the MEG vessel 138 is used to flush one or more of the filters 124/126, the MEG will entrain or dissolve HTF material, and potentially other impurities, deposited on the filter medium in the filters 124/126, becoming contaminated in the process. The contaminated MEG exits the filters 124/126 into the manifold 134 and flush outlet line 146. The contaminated MEG can be recovered in this case by closing the flush exhaust valve 148 and opening flush recycle valve 168. The flush recycle valve 168 admits flush exhaust material into a flush recycle line 150 that carries flush material back to a flush feed point 172 of the vessel 102. When purified MEG is used as the flush material, flowing the resulting contaminated MEG through the flush recycle valve 168 and the flush recycle line 150 to the flush feed point 172 recovers the MEG to the vaporization vessel 102, avoiding loss of valuable MEG. The contaminants in the contaminated MEG are mostly HTF fluid, which returns to its source at the vessel 102. When the flush recycle line 150 is in use, the flush exhaust valve 148 can be closed.

A sensor 170 is coupled to the stream flowing into the purification section 180 to monitor composition of the stream. The sensor 170 is a composition sensor that detects quantity of residual HTF in the stream flowing to the purification section. The composition detected by the sensor 170 can be used to detect breakthrough of any of the filters 124/126 in service. The composition detected by the sensor 170 can also be used to predict future breakthrough of any of the filters 124/126 in service. Instead of, or in addition to, the composition sensor 170, a pressure drop sensor may be disposed across the filters 124/126 to detect filter plugging due to adsorbed HTF on the filter material. Here, a single pressure drop sensor 174 is disposed across the two filters 124/126 to detect total pressure drop across the two filters, regardless which is in service. Alternately, a pressure drop sensor can be disposed across each filter individually. Together, the pressure drop sensor 174, along with the composition sensor 170, can be used to monitor filter performance.

The apparatus of FIG. 1 provides filtration of vaporized MEG from a vaporization vessel, with the flexibility to maintain and regenerate filter materials after a period of use. Two flush capabilities are provided to flush the filter media, thus removing deposited impurities without opening the filters. Two fluids, a flush fluid specifically chosen for flushing the filters, and purified MEG product fluid, can be used to flush the filters in the apparatus of FIG. 1, thus providing improved regeneration of filter media, and recovery of MEG used for filter flushing. The apparatus of FIG. 1 further provides the flexibility to liquefy the vaporizer overhead prior to, or after, filtering.

Figure 2:
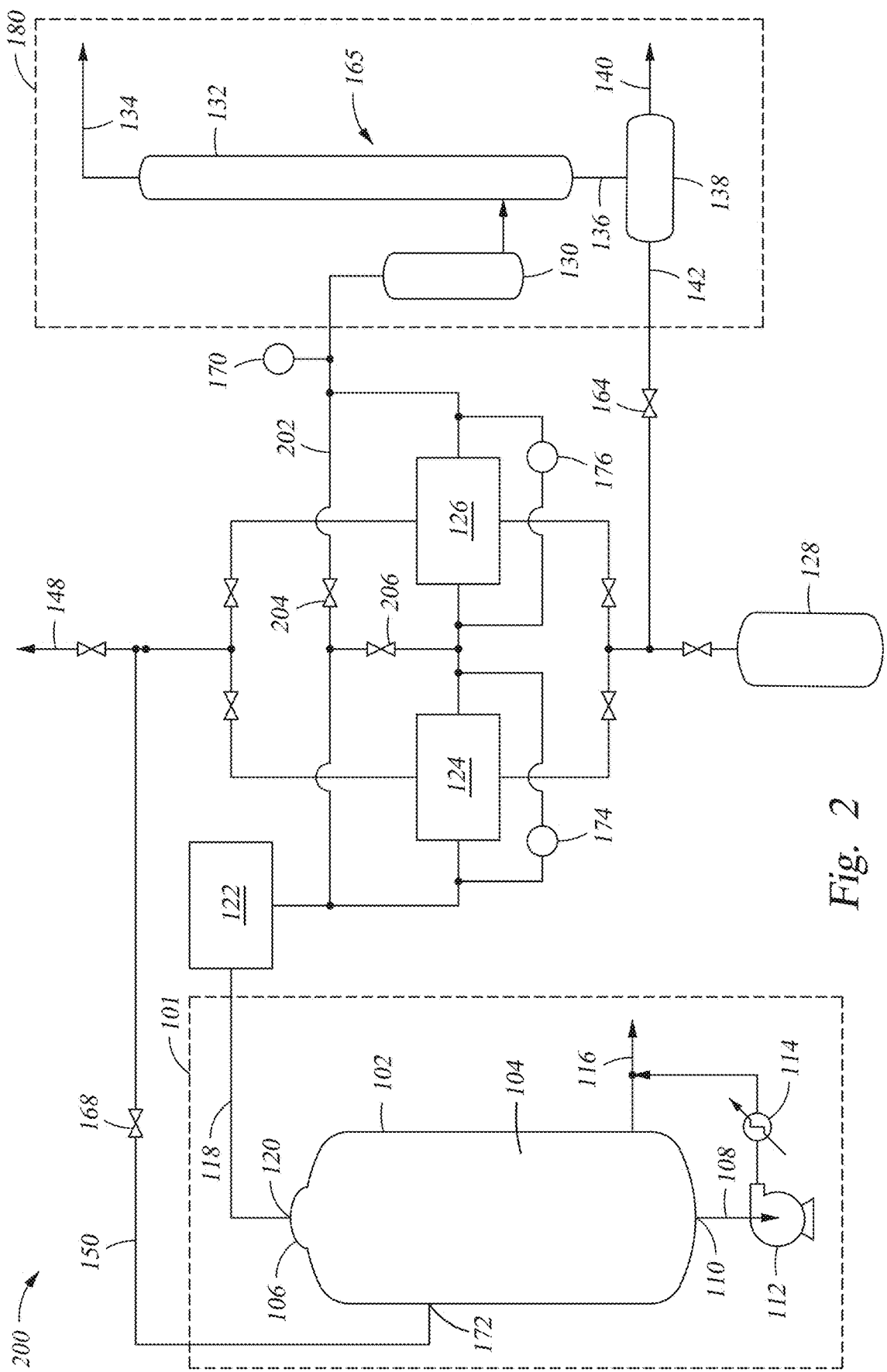
FIG. 2 is a process diagram of an apparatus according to another embodiment.

FIG. 2 is a process diagram of an apparatus 200 according to another embodiment. The apparatus 200 features the vaporization section 101 and the purification section 180. The liquefier 122 and filters 124 and 126 are arranged differently in FIG. 2. Here, the liquefier 122, filter 124, and filter 126 are arranged in series. A recycle line 202 is provided to recycle flow of liquefied rich MEG through the filters 124 and 126. Recycling the rich MEG improves utilization of the filter material to remove HTF from the rich MEG. A recycle valve 204 can be operated to start, stop, and control flow of rich MEG through the recycle line 202. The recycle line 202 carries rich MEG from a point downstream of the filters 124 and 126 to a point upstream of the filters 124 and 126. A partial recycle valve 206 can be opened to flow rich MEG to a location between the first filter 124 and the second filter 126. In this way, operation of the filters 124/126 can be arranged as series/parallel. Using the apparatus 200, utilization of the two filters 124 and 126 can be controlled based on performance of the two filters, one filter being used more than the other or both filters being used equally. The flush source 128 is coupled to the two filters 124/126 in parallel, with valving to isolate the filters for flushing, if desired. The purified MEG stream is also coupled to the flush system, as in FIG. 1. In this case, two pressure drop sensors 174 and 176 are used to monitor performance of the two filters 124/126 operating in series.

Figure 3:
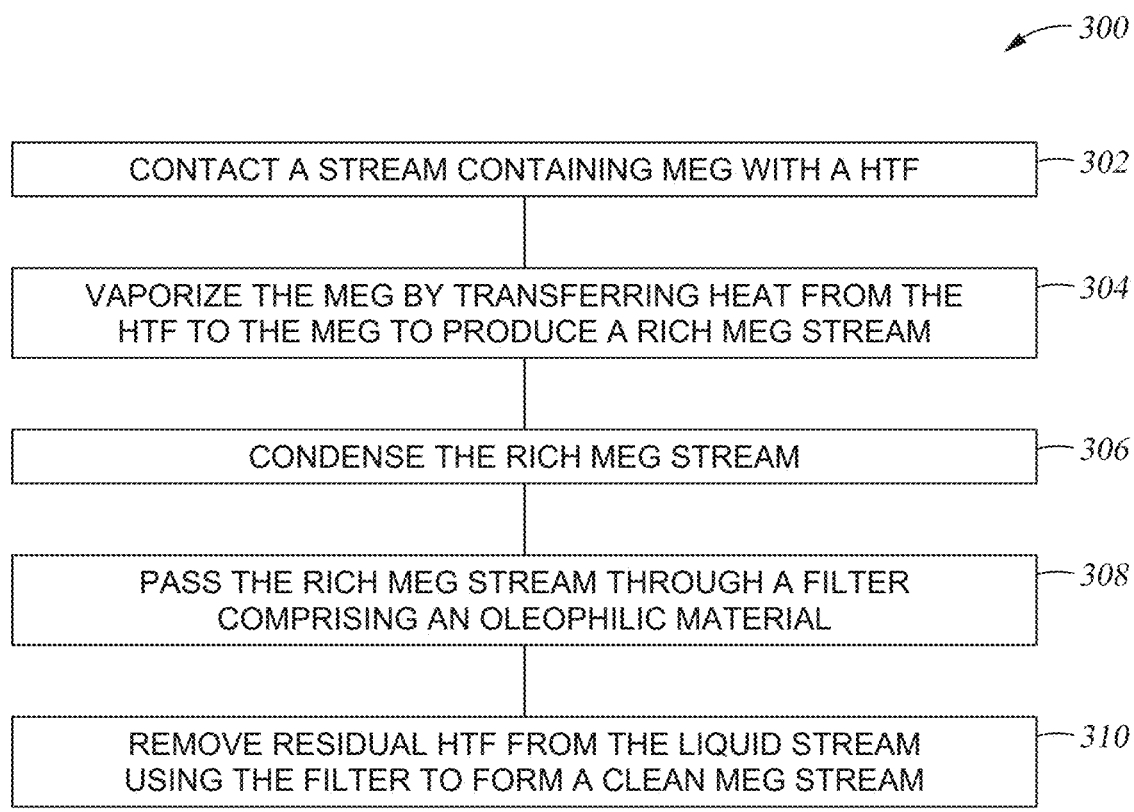
FIG. 3 is a flow diagram summarizing a method according to another embodiment.

FIG. 3 is a flow diagram summarizing a method 300 according to another embodiment. The method 300 is a method of processing a MEG concentrate stream from a hydrocarbon processing plant. The MEG concentrate stream is subjected to vaporization to remove coarse impurities, filtration to remove finer impurities, and finally distillation to remove miscible impurities. At 302, a stream containing MEG is contacted with an HTF. The stream containing MEG can be a MEG concentrate stream from a hydrocarbon processing facility. The HTF is maintained at a temperature at or above the bubble point of MEG in the stream containing MEG, and below a decomposition temperature of the MEG. The temperature is typically around 165° C., but may be lower if the vaporization process is operated under reduced pressure, or vacuum.

At 304, MEG is vaporized by transferring heat from the HTF to the MEG. Typically, the stream containing MEG directly contact the HTF as fluid contact. In other words, the stream containing MEG is injected into the HTF such that thermal transfer occurs directly across a liquid-liquid interface between the MEG stream and the HTF. MEG vaporizes from the stream containing MEG, forming a gas phase in the liquid mixture. The gas containing MEG escapes the liquid phase into the vapor phase. The vaporized MEG forms a rich MEG stream with miscible impurities and fine impurities. The HTF is recirculated through a heating system to maintain the HTF at a vaporization temperature. Impurities can be removed from the HTF by filtration or other means. For example, a portion of the recirculating HTF can be routed to a solids removal unit optionally featuring filtration, density separations, or other separation means.

At 306, the rich MEG stream from the vaporization operation is condensed. The resulting liquid stream contains liquid MEG along with other liquid impurities. Water is mixed in a single phase with MEG, while some trace quantities of HTF may be entrained as an immiscible liquid phase.

At 308, the liquefied rich MEG stream is passed through a filter comprising an oleophilic filter material. The oleophilic material is selective to the HTF, and preferentially adsorbs the HTF from the liquid stream, immobilizing the HTF and removing the HTF from the liquid MEG-containing stream. Thus, at 310, the HTF is thus effectively separated from the MEG, resulting in a clean MEG stream that can be separated to yield purified MEG.

Filter materials described above may be used in the apparatus 200, as well. Flushing operations described above can also be performed using the flushing materials and methods described above. Following flushing with the low polarity aprotic solvent, the filter material may be flushed with purified MEG obtained from a downstream MEG purification unit. Filtering with purified MEG can remove most of the flush material bearing the HTF from the filter, the preparing the filter to be put back into service. The clean MEG stream exiting the filter can be distilled, for example, to separate water from the MEG. Other separation processes, such as liquid extraction, vacuum extraction, and differential permeability extraction can be used instead of, or in addition to, distillation.

While the foregoing is directed to embodiments of the subject matter of this disclosure, other and further embodiments of the present disclosure may be devised without departing from the basic scope thereof, and the scope thereof is determined by the claims that follow.

What is claimed is:

1. A method, comprising:
   directly contacting a stream containing monoethylene glycol (MEG) with a heat transfer fluid (HTF);
   vaporizing the MEG by transferring heat from the HTF to the MEG to produce a rich MEG stream;
   condensing the rich MEG stream;
   passing the rich MEG stream through a filter comprising an oleophilic material; and
   removing residual HTF from the rich MEG stream using the filter to form a clean MEG stream.

2. The method of claim 1, wherein the oleophilic material is a filter element having a form selected from the group consisting of a mesh, a permeable sheet, and a powder.

3. The method of claim 1, wherein the oleophilic material is an aromatic resin, a polyacrylate, or a mixture thereof.

4. The method of claim 1, further comprising detecting an amount of the HTF in the clean MEG stream.

5. The method of claim 4, further comprising determining an end point based on the amount of the HTF in the clean MEG stream.

6. The method of claim 5, further comprising, upon determining the end point, flushing the filter using a fluid miscible with the HTF.

7. The method of claim 6, wherein the fluid is a low polarity aprotic solvent.

8. The method of claim 1, further comprising separating water from the clean MEG stream to form a purified MEG stream.

9. The method of claim 8, further comprising:
   detecting an amount of the HTF in the clean MEG stream;
   determining an end point based on the amount of the HTF in the clean MEG stream;
   upon determining the end point, flushing the filter using a low polarity aprotic solvent; and
   flushing the filter using a portion of the purified MEG stream.

10. A method, comprising:
    mixing a MEG concentrate stream with an HTF to form a vaporization mixture;
    vaporizing a rich MEG stream from the vaporization mixture in a vessel;
    passing the rich MEG stream through a filter comprising a filter material selective to the HTF in a filter flow direction;
    immobilizing the HTF on the filter material to form a clean MEG stream;
    detecting an amount of the HTF in the clean MEG stream;

determining a filter efficiency based on the amount of the HTF in the clean MEG stream;
determining an end point based on the filter efficiency; and
upon determining the end point, flushing the filter material by flowing a low polarity aprotic solvent through the filter in a flush flow direction.

11. The method of claim 10, further comprising separating water from the clean MEG stream to form a purified MEG stream, and after flushing the filter material using the low polarity aprotic solvent, flushing the filter material using a portion of the purified MEG stream.

12. The method of claim 10, wherein the flush flow direction is opposite to the filter flow direction.

13. The method of claim 10, wherein the flush flow direction is transverse to the filter flow direction.

14. The method of claim 10, wherein the filter material is a polystyrene resin.

15. The method of claim 10, wherein the low polarity aprotic solvent is selected from the group consisting of linear, branched, and cyclic pentanes, hexanes, heptanes, octanes, and nonanes, benzene, toluene, xylene, dioxane, anisole, dimethylamine, diethyl ether, methyl t-butyl ether, chloromethane, dichloromethane, chloroform, and carbon tetrachloride.

16. The method of claim 10, wherein passing the rich MEG stream through the filter comprises recycling a portion of the rich MEG stream through the filter.

17. The method of claim 16, wherein the filter comprises at least two filters, and recycling the portion of the rich MEG stream through the filter comprises recycling the portion of the rich MEG stream through all the filters.

18. A method, comprising:
mixing a MEG concentrate stream with an HTF to form a vaporization mixture;
vaporizing a rich MEG stream from the vaporization mixture in a vessel;
passing the rich MEG stream through a plurality of filters comprising a filter material selective to the HTF in a filter flow direction;
recycling a portion of the rich MEG stream through one or more of the plurality of filters;
immobilizing the HTF on the filter material to form a clean MEG stream;
detecting an amount of the HTF in the clean MEG stream;
determining a filter efficiency based on the amount of the HTF in the clean MEG stream;
determining an end point based on the filter efficiency; and
upon determining the end point, flushing the filter material by flowing a low polarity aprotic solvent through the filters in a flush flow direction.

19. The method of claim 18, wherein the filter material is a polystyrene resin.

20. The method of claim 18, wherein the filter material is a polyacrylate resin.

* * * * *